United States Patent
Doge et al.

(10) Patent No.: US 7,081,362 B2
(45) Date of Patent: Jul. 25, 2006

(54) DEVICE AND METHOD FOR CULTIVATION

(75) Inventors: Fuyuki Doge, Tokyo (JP); Katsuo Isaka, Tokushima (JP); Akikuni Hara, Tokyo (JP)

(73) Assignee: Hakuju Institute for Health Science Co., Ltd. (JP)

( * ) Notice: Subject to any disclaimer, the term of this patent is extended or adjusted under 35 U.S.C. 154(b) by 0 days.

(21) Appl. No.: 10/476,778

(22) PCT Filed: Jun. 25, 2002

(86) PCT No.: PCT/JP02/06320

§ 371 (c)(1),
(2), (4) Date: Mar. 15, 2004

(87) PCT Pub. No.: WO03/000838

PCT Pub. Date: Jan. 3, 2003

(65) Prior Publication Data

US 2004/0235151 A1    Nov. 25, 2004

(30) Foreign Application Priority Data

Jun. 25, 2001  (JP) .............................. 2001-191899

(51) Int. Cl.
*C12M 1/12* (2006.01)
(52) U.S. Cl. ................ 435/297.5; 204/403.01
(58) Field of Classification Search ............. 435/173.1, 435/285.2, 297.1, 297.5; 204/403.01
See application file for complete search history.

(56) References Cited

U.S. PATENT DOCUMENTS

| | | | | | |
|---|---|---|---|---|---|
| 4,321,322 | A | * | 3/1982 | Ahnell | 205/777.5 |
| 4,970,154 | A | * | 11/1990 | Chang | 424/93.21 |
| 5,972,694 | A | * | 10/1999 | Mathus | 435/288.4 |

FOREIGN PATENT DOCUMENTS

| | | |
|---|---|---|
| JP | 63-188385 | 8/1988 |
| JP | 03-050244 | 3/1991 |
| JP | 06-121684 | 5/1994 |
| JP | 08-224080 | 9/1996 |
| WO | WO 89/03876 | 5/1989 |

* cited by examiner

*Primary Examiner*—David Redding
(74) *Attorney, Agent, or Firm*—Cook, Alex, McFarron, Manzo, Cummings & Mehler, Ltd.

(57) ABSTRACT

A culture apparatus and cultivation method are provided which enable liquid materials such as cells or blood plasma to be evenly cultivated by making current density uniform.

The culture apparatus comprises a vessel 14 having a predetermined capacity with a lower electrode 16 placed on its bottom, a cover 17 disposed in a vertically opposite direction to the vessel 14 for hermetically sealing the vessel 14 by covering the vessel 14 from above and comprising an upper electrode 18 provided opposite to the lower electrode 16, a culturing member 20 fit into the vessel 14 comprising almost in its center a hollow 21 that has a capacity made by a predetermined cross section area; a filter 25 provided between the vessel 14 and the culturing member 20, and a power source device for applying a predetermined voltage to the lower electrode 16 and the upper electrode 18 to let a current flow between the both electrodes.

10 Claims, 3 Drawing Sheets

DEVICE AND METHOD FOR CULTIVATION

BACKGROUND OF THE INVENTION (i) Field of the Invention

The present invention relates to a culture apparatus and a cultivation method for cultivating liquid materials such as cells or blood plasma in a culture medium.

(ii) Description of the Related Art

FIG. 7 is a schematic view of a conventional horizontal cell culture apparatus. In the Figure, a current of a function generator 1 flows to connection terminals 6 of electrodes provided at both ends in the culture apparatus via an amplifier 2 and an ammeter 3. The culture apparatus applies a voltage directly to both sides of a culture tub 4 or between the electrodes via an agarose 5 for removing contaminants, and thus applies the current to the liquid materials such as cells or blood plasma in a culture solution. A current value that flows is derived by an oscilloscope 7. FIG. 8 is a schematic view of another culture apparatus. In this Figure, in the same way as above, a current source is connected to platinum electrodes 9 covered with insulators 10, and the platinum electrodes 9 are directly inserted into the culture medium to apply the current to the liquid materials such as the cells or blood plasma in the culture medium.

In the conventional culture apparatus, the current flows in a horizontal direction. For this reason, even with uniform current density, current stimuli that are applied to the liquid materials such as the cells or the blood plasma vary between the floating cells and adsorbent cells, because of shapes of the cells and precipitated ingredients of the culture medium. In addition, because chemical reactions occurring in the vicinity of electrode surfaces affect the cultivation of the liquid materials such as the cells or the blood plasma, a buffer such as the agarose is stuck on the electrode surfaces. Further, depending upon the kinds of liquid materials such as the cells or the blood plasma to be cultivated or for identical testing of the liquid materials such as the cells or the blood plasma, the amount of culture medium to be used is varied. This presents a drawback that many kinds of culturing plates are required.

SUMMARY OF THE INVENTION

The present invention has been proposed in order to solve such a drawback that has conventionally been presented. An object of the invention is to provide a culture apparatus and cultivation method that enable liquid materials such as cells or blood plasma to be evenly cultivated with current density uniformed by causing a current to flow in a vertical direction (vertical type).

A culture apparatus according to the present invention comprises: a vessel having a predetermined capacity with a lower electrode placed on its bottom; a cover disposed in a vertically opposite direction to said vessel for hermetically sealing said vessel by covering said vessel from above and comprising an upper electrode provided opposite to said lower electrode; a culturing member fit into said vessel comprising almost in its center a hollow that has a capacity made by a predetermined cross section area; a filter provided between said vessel and said culturing member; and a power source device for applying a predetermined voltage to said lower electrode and said upper electrode to let a current flow between said both electrodes.

The culture apparatus according to the present invention comprises: a culture vessel having a predetermined capacity with a lower electrode placed on its bottom; a cover disposed in a vertically opposite direction to said vessel for hermetically sealing said culture vessel by covering said culture vessel from above and comprising an upper electrode provided opposite to said lower electrode; a holding member provided being fixed to said vessel; a filter having a predetermined cross section area provided between said vessel and said holding member; and a power source device for applying a predetermined voltage to said lower electrode and said upper electrode to let a current flow between said both electrodes.

The culture apparatus according to the present invention is for cultivating cells in a culture medium by applying a predetermined voltage between a lower electrode and an upper electrode to let a current flow between said both electrodes. The apparatus comprises current density generating means for uniforming current density in the culture medium by causing the current to flow in a vertical direction and thus applying the uniform current density to a cultivated material.

Said lower electrode is provided in a concavity made on the bottom of said vessel. Said upper and lower electrodes are made from spiral platinum. Agarose is applied to opposing surfaces of said upper and lower electrodes. Said filter is a transparent membrane film or a transparent collagen film. Said culturing member comprises a pair of bores for letting in tweezers that are for taking a member in and out.

The culture apparatus according to the present invention is for cultivating a cultivated material in a culture medium by applying a predetermined voltage between a lower electrode and an upper electrode to let a current flow between said both electrodes. In the apparatus, current density in the culture medium is uniformed by causing the current to flow in a vertical direction and thus the uniformed current density is applied to the cultivated material.

The culture apparatus according to the present invention is for cultivating a cultivated material in a culture medium by applying a predetermined voltage between a lower electrode and an upper electrode to let a current flow between said both electrodes. In the apparatus, current density in the culture medium is variable by causing the current to flow in a vertical direction and thus the current density is applied variably to the cultivated material.

DETAILED DESCRIPTION OF THE PREFERRED EMBODIMENT

Figure 1:
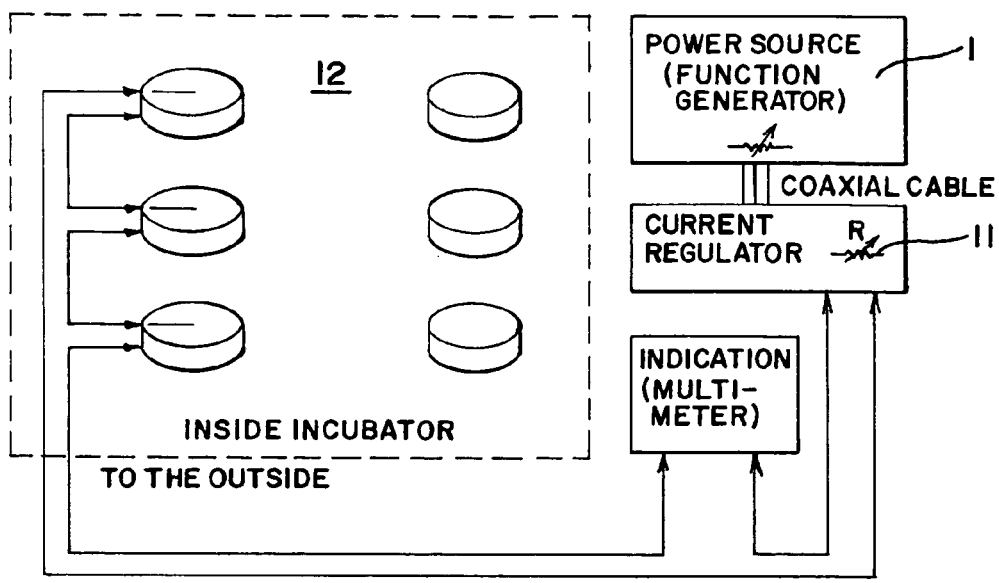
FIG. 1 is a schematic arrangement plan showing a culture apparatus according to the present invention.

One embodiment of a culture apparatus according to the present invention will hereafter be described with reference to the accompanying drawings. FIG. 1 schematically shows the culture apparatus. As described later with an example of cell cultivation, the culture apparatus can be applied to liquid materials such as blood plasma besides cells. A signal waveform generated by a function generator 1 serves as a current source via a current regulator 11, and this is connected in series to a group of culture apparatuses 12. The current flowing in a closed circuit is measured and indicated by an ammeter.

Figure 2:
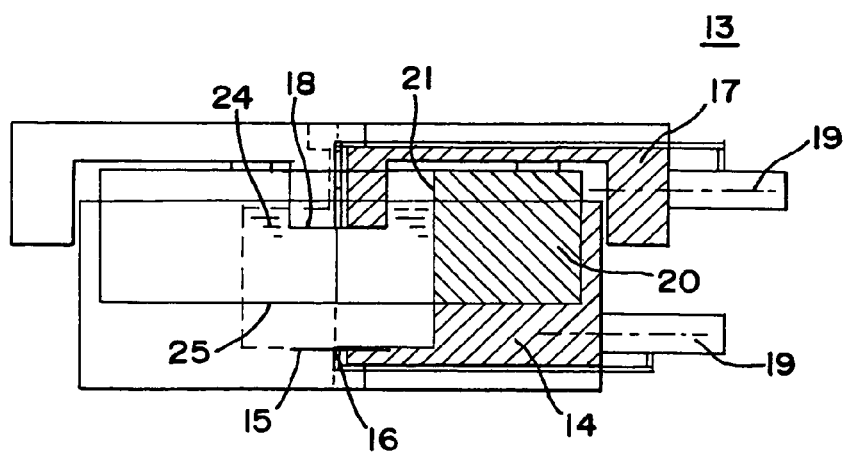
FIG. 2 is a schematic diagram showing the culture apparatus according to the present invention.

FIG. 2 is a schematic diagram showing a constitution of a culture apparatus 13. In the culture apparatus shown in the Figure, a reference numeral 14 indicates a cylindrical vessel whose inside is hollow having a predetermined capacity. The vessel 14 comprises a concavity 15 almost in the center of its bottom. A lower electrode 16 is provided in the concavity. The vessel 14 is covered with a cover 17 from above. The cover 17 comprises an upper electrode 18 in a position opposite to the lower electrode. The upper and lower electrodes 18 and 16 are formed of spiral or disk-shaped platinum electrodes. The electrodes 18 and 16 are each connected to a current source (not shown) via connection terminals 19. With the electrodes that are spiral, it is possible to observe the shapes of the cells from the openings. In this way, a predetermined voltage is applied to the lower electrode 16 and the upper electrode 18 to let the current flow between the electrodes. In addition, the lower-side vessel 14 and the cover 17 are disposed in a vertical direction (vertical type). Agarose may be applied to the surfaces of the upper and lower electrodes 18 and 16. By applying the agarose on the electrode surfaces, it is possible to reduce the effects of chemical reactions in the vicinity of the electrode surfaces to the cells.

Figure 3:
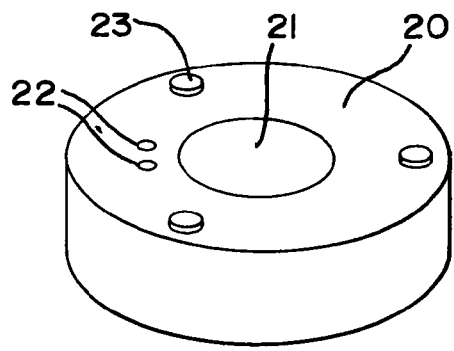
FIG. 3 is a schematic diagram showing a culturing member of the culture apparatus according to the present invention.

A reference numeral 20 is a cylindrical culturing member that is fit into the vessel 14 and that comprises almost in its center a hollow 21 having a predetermined capacity for accommodating a culture medium in which the cells to be cultivated are put. The hollow 21 houses almost in its center the upper electrode 18 of the cover 17. As shown in FIG. 3, the culturing member 20 comprises bores 22 on its upper surface so that a member 20 that is fit into the vessel 14 may easily be taken out. It is thereby easy to remove the middle member 20 by picking it up with tweezers that are put into the bores 22. A reference numeral 23 indicates a projection for an opening that prevents the culture medium from drying. A reference numeral 24 indicates the culture medium.

Furthermore, between the culturing member 20 and the vessel 14, a filter 25 is provided. The filter 25 prevents the cells put in the culture medium 24 in the hollow 21 of the culturing member 20 from falling on the lower electrode 16 of the vessel 14 to contact the electrode 16. The filter 25 is formed of a transparent membrane, and it has a pore size of approximately 0.4 micron and a thickness of approximately 8 microns. An aperture between the culturing member 20 and the vessel 14 is set to be less than 0.2 mm so that the culture medium 24 poured in the hollow 21 of the culturing member 20 would not flow out of the culturing member 20.

Figure 4:
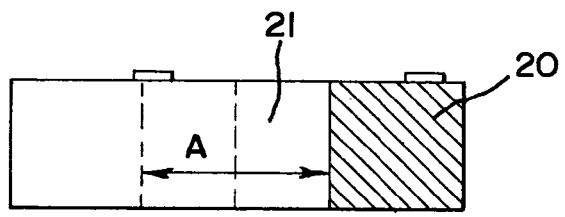
FIG. 4 is a sectional view showing the culturing member of the culture apparatus according to the present invention.
Figure 5:
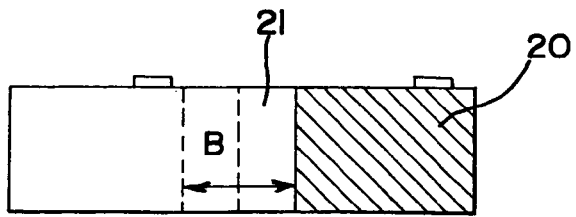
FIG. 5 is a sectional view showing another culturing member of the culture apparatus according to the present invention.

When a large amount of culture medium is needed, as shown in FIG. 4, a cross section area A of the hollow 21 of the culturing member 20 is enlarged to have a larger capacity. Contrarily, when a reduced amount of culture medium is needed, as shown in FIG. 5, a cross section area B (A>B) of the hollow 21 of the culturing member 20 is reduced to have a smaller capacity. In this way, by the provision of a plurality of culturing members 20 having different cross section areas of the hollows 21, the amount of culturing medium can easily be varied merely by changing the culturing members 20. As a result, it is possible to quickly and easily adapt to the varied amount of culture medium that depends upon the kind of cells to be cultivated. Only by replacing the culturing members 20, it is possible to deal with several kinds of culture medium amounts such as 1 ml or 3 ml.

The culture medium 24 is poured in the concavity 15 of the vessel 14 in advance. The transparent membrane filter 25 is provided between the vessel 14 and the culturing member 20. Then, the culture medium 24 containing the cells to be cultivated is filled up to the position where the upper electrode 18 is soaked. A predetermined voltage is applied between the upper electrode 18 and the lower electrode 16 to let the current flow. Current density in the culture medium 24 can be derived by subtracting a current value that has flown from the cross section area of the hollow 21 of the culturing member 20. By causing the current to flow in a vertical direction, the current density in the culture medium 24 can be uniform, which makes it possible to apply the uniform current density to the cells. Further, the current density in the culture medium 24 can be variable with a constant current value and with the cross section area variable by providing a plurality of culturing members 20.

In order to cultivate the cells, the predetermined voltage is applied between the lower electrode 16 and the upper electrode 18 to make the current flow in the direction vertical to the cells between the electrodes and to apply the uniform current density to the cells.

Figure 6:
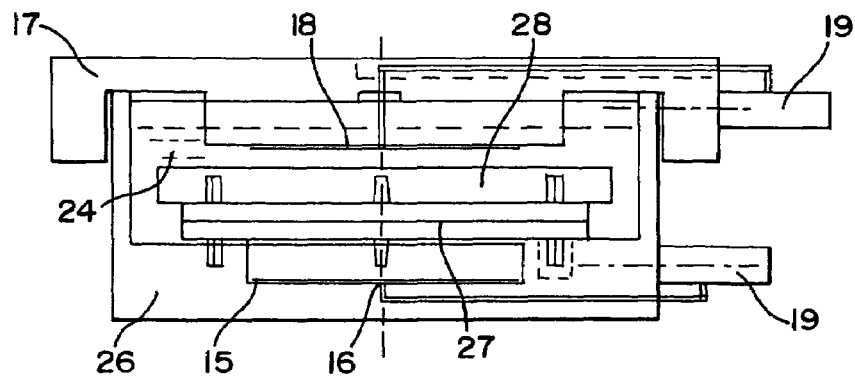
FIG. 6 is a schematic diagram showing another culture apparatus according to the present invention.
Figure 7:
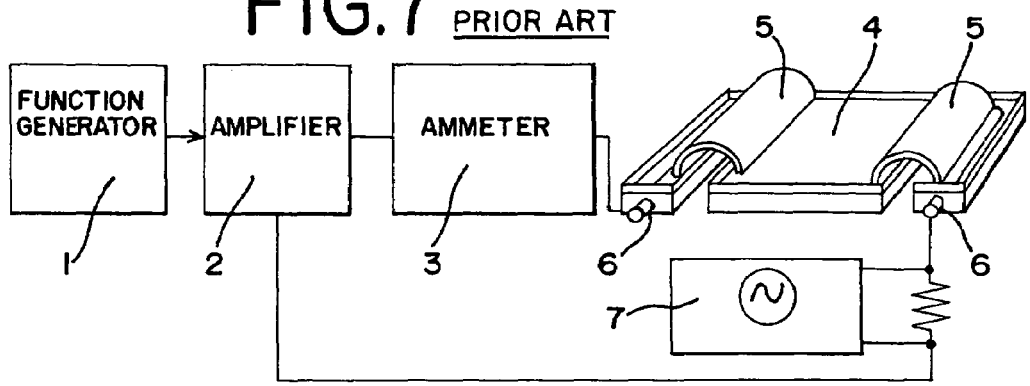
FIG. 7 is a schematic diagram showing a conventional horizontal culture apparatus.
Figure 8:
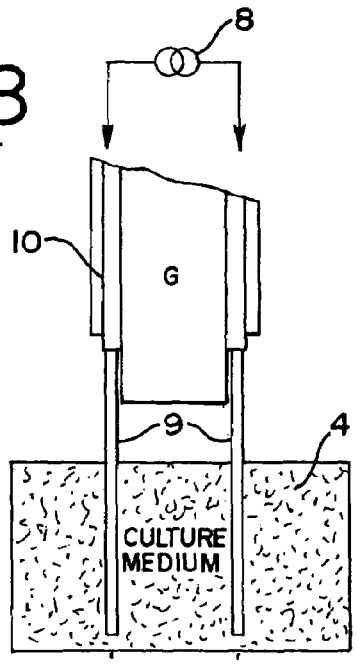
FIG. 8 is a schematic diagram showing another conventional culture apparatus.

FIG. 6 shows another embodiment of the culture apparatus. As described later with an example of cell culture, the culture apparatus can be applied to the liquid materials such as the blood plasma in addition to the cells. In the culture apparatus, a reference numeral 26 indicates a culture vessel that accommodates the culture medium 24 for cultivating the cells. The vessel 26 is a cylindrical vessel whose inside is hollow. The vessel 26 comprises the concavity 15 almost in the center of its bottom, and the lower electrode 16 is provided in the concavity 15. The vessel 26 is covered with the cover 17 from above. The cover 17 comprises the upper electrode 18 in a position opposite to the lower electrode 16. The upper and lower electrodes 18 and 16 are spiral platinum electrodes. The electrodes 18 and 16 are each connected to the current source (not shown) via the connection terminals 19. In this way, the predetermined voltage is applied to the lower electrode 16 and the upper electrode 18 to let the current flow between the both electrodes.

Furthermore, the culture vessel 26 and the cover 17 are disposed in the vertical direction (vertical type). Inside the culture vessel 26, a filter 27 using a transparent collagen film and a holding member 28 for preventing the filter 27 from floating up are provided. In this way, the filter 27 prevents the cells in the culture medium 24 from falling on the lower electrode 16. The filter 27 is provided between the lower-side vessel 26 and the holding member 28, and is prevented from floating up by the culture medium 24 put in the vessel 26. The current density in the culture medium 24 can be derived by subtracting a current value that has flown from the cross section area of the filter 27 formed of the transparent collagen film. Further, when the current value is constant, the current density can be applied variably to the cells by making the cross section area of the filter 27 that is formed of the transparent collagen film variable.

In order to cultivate the cells, the predetermined voltage is applied between the lower electrode 16 and the upper electrode 18 to make the current flow in the direction vertical to the cells between the electrodes and to apply the uniform current density to the cells. The present invention is particularly suitably used for a cell cultivation test.

In the culture apparatus and cultivation method according to the present invention, the current density is made uniform by causing the current to flow in the vertical direction (vertical type), thus making it possible to cultivate the liquid materials such as the cells or blood plasma evenly.

As described above, the culture apparatus and cultivation method of the present invention is used for cultivating the liquid materials such as the cells or blood plasma.

What is claimed is:

1. A culture apparatus comprising:
  a vessel having a predetermined capacity with a lower electrode placed on its bottom;
  a cover disposed in a vertically opposite direction to said vessel for hermetically sealing said vessel by covering said vessel from above and comprising an upper electrode provided opposite to said lower electrode;
  a culturing member fit into said vessel comprising almost in its center a hollow that has a capacity made by a predetermined cross section area;
  a filter provided between said vessel and said culturing member; and
  a power source device for applying a predetermined voltage to said lower electrode and said upper electrode to let a current flow between said both electrodes.

2. A culture apparatus comprising:
  a culture vessel having a predetermined capacity with a lower electrode placed on its bottom;
  a cover disposed in a vertically opposite direction to said vessel for hermetically sealing said culture vessel by covering said culture vessel from above and comprising an upper electrode provided opposite to said lower electrode;
  a holding member provided being fixed to said vessel;
  a filter having a predetermined cross section area provided between said vessel and said holding member; and
  a power source device for applying a predetermined voltage to said lower electrode and said upper electrode to let a current flow between said both electrodes.

3. The culture apparatus according to claim 1, wherein said lower electrode is provided in a concavity made on the bottom of said vessel.

4. The culture apparatus according to claim 1, wherein said upper and lower electrodes are made from spiral platinum.

5. The culture apparatus according to claim 1, wherein agarose is applied to opposing surfaces of said upper and lower electrodes.

6. The culture apparatus according to claim 1, wherein said filter is a transparent membrane film or a transparent collagen film.

7. The culture apparatus according to claim 1, wherein said culturing member comprises a pair of bores for letting in tweezers that are for taking a member in and out.

8. The culture apparatus according to claim 2, wherein said upper and lower electrodes are made from spiral platinum.

9. The culture apparatus according to claim 2, wherein agarose is applied to opposing surfaces of said upper and lower electrodes.

10. The culture apparatus according to claim 2, wherein said filter is a transparent membrane film or a transparent collagen film.

* * * * *